(12) United States Patent
Bajgrowicz et al.

(10) Patent No.: US 7,550,417 B2
(45) Date of Patent: Jun. 23, 2009

(54) OXYGEN-CONTAINING TRI- OR TETRA-CYCLIC TERPENOID COMPOUNDS

(75) Inventors: Jerzy A. Bajgrowicz, Zürich (CH); Iris Frank, Fällanden (CH)

(73) Assignee: Givandan SA, Vernier (CH)

( * ) Notice: Subject to any disclaimer, the term of this patent is extended or adjusted under 35 U.S.C. 154(b) by 0 days.

(21) Appl. No.: 12/065,390

(22) PCT Filed: Sep. 8, 2006

(86) PCT No.: PCT/CH2006/000484

§ 371 (c)(1),
(2), (4) Date: Mar. 10, 2008

(87) PCT Pub. No.: WO2007/030963

PCT Pub. Date: Mar. 22, 2007

(65) Prior Publication Data

US 2008/0248990 A1    Oct. 9, 2008

(30) Foreign Application Priority Data

Sep. 14, 2005 (GB) .................. 0518729.9
Oct. 28, 2005 (GB) .................. 0521929.0

(51) Int. Cl.
*C11D 3/50* (2006.01)
(52) U.S. Cl. .................. 510/104; 512/14; 568/823; 568/828
(58) Field of Classification Search .................. 510/104; 512/14; 568/823, 828
See application file for complete search history.

(56) References Cited

U.S. PATENT DOCUMENTS 4,100,110 A    7/1978    Ansari et al.

FOREIGN PATENT DOCUMENTS

DE    2535576 A1    2/1976
FR    228110 A    3/1976
FR    2281100 A1 *    3/1976

OTHER PUBLICATIONS

H. Chen et al., Huaxue Shijie 1999, vol. 40, issue 4, pp. 190-193. Jun. 1999. English abstract only.*
Article to accompany CAS Abstract Acc. No. 1997:188841: Journal of Chemical Research, "The Addition to 1,5-Dimethyl-1-vinylhex-4-enyl (Linalyl) Acetate, Cholest-5-en-3B-yl Acetate, and 1,3,4,5,6,7-Hexahydro-1,1,5,5-tetra-methyl-2H-2x, 4ax-methanonaphthalene (Isolongifolene) or Organic Radicals generated by Manganese (iii) Oxidation, Induced Allylic Oxidation" Synopses 1977, vol. (3), McQuillin et al., p. 61.
CAS Abstract Acc. No. 2000: 156356 (of the article for) Jiangxi Shifan Daxue Xuebao, "Ziran Kexueban" 1999, vol. 23 (4), Chen et al., pp. 356-359.
Article to accompany CAS Abstract Acc. No. 1999:381098: Huaxue Shijie, "Study on the Condensation Reactions of Formylisolongifolene with Ketones" 1999, vol. 40(4)_, Chen Huizong et al., pp. 190-193.
English Language Abstract for FR2281100 taken from Google Translate.
GB Search Report for Application No.: GB0518729.9 dated Feb. 8, 2006.

* cited by examiner

*Primary Examiner*—John R Hardee
(74) *Attorney, Agent, or Firm*—Norris McLaughlin & Marcus, PA

(57) ABSTRACT

The use as fragrance ingredient of a compound of formula (I)

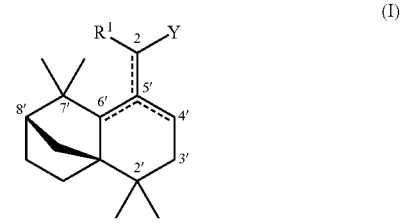

(I)

wherein $R^1$ and Y have the same meaning as given in the description, and fragrance applications comprising them.

8 Claims, No Drawings

OXYGEN-CONTAINING TRI- OR TETRA-CYCLIC TERPENOID COMPOUNDS

This is an application filed under 35 USC 371 of PCT/CH2006/000484.

The present invention refers to a novel class of oxygen-containing tri- and tetra-cyclic terpenoids having woody, ambery and musky odor notes and their use as odorants. This invention relates furthermore to a method of their production and fragrance compositions comprising them.

In the modern perfumery woody, ambery and musky notes play a decisive role. They form the foundation of a lot of perfumes, and it is difficult to imagine a perfume without any woody or ambery notes. Surprisingly it has now been found that certain oxygen containing tri- and tetra-cyclic terpenoids constitute very powerful ambery, woody and musky odorants.

Many oxygen-containing terpenoids with an isolongifolane ring system are known, some of which have characteristic odor notes and thus are particularly suitable for use in perfumery, such as Folenox (A), Piconia (B), Ysamber®K (C) and acetylisolongifolene (D), whereas, on the other hand, a large number of terpenoids are known which have no or essentially no olfactory properties. However, it has never been possible to draw a complete correlation between structure and odor, and therefore one cannot generally predict which compounds will possess a useful or pleasing odor, or what the particular odor description of any given compound will be.

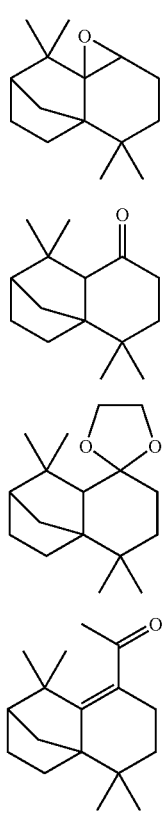

The compounds derived from isolongifolene known from the art have in common that the osmophoric center, namely the oxygen atom, is linked either via a C1-spacer group or directly to the cyclic ring system, i.e. the lipophilic part of the molecule. Surprisingly it has been found that when the distance between the osmophoric center and the lipophilic center of the molecule is bigger, there may be obtained very powerful molecules possessing a very high substantivity (odour longevity) when applied on animated or unanimated surfaces, such as fabrics, hairs and skin.

Accordingly, the present invention refers in one of its aspects to a fragrance composition comprising an oxygen-containing tri- or tetra-cyclic terpenoid of formula (I)

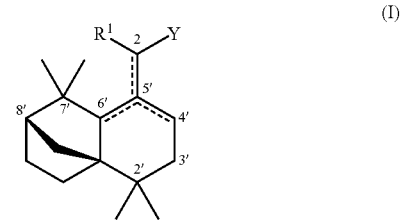

wherein $R^1$ is hydrogen or $C_1$-$C_3$ alkyl, e.g. methyl, ethyl or isopropyl;

Y is a monovalent residue selected from the group consisting of —$CR^2O$ and —$CHR^2OR^3$, wherein $R^2$ is hydrogen or $C_1$-$C_3$ alkyl, e.g. methyl, ethyl or isopropyl; and $R^3$ is hydrogen or $C_1$-$C_3$ alkyl, e.g. methyl, ethyl or isopropyl; or Y is a divalent residue of the formula —$CHR^2OCHR^2$— forming together with the carbon atoms C-2, C-5' and C-4' a six-membered ring system, wherein $R^2$ is hydrogen or methyl;

and the bonds between C-5' and C-6', C-4' and C-5', and C-2 and C-5' are single bonds, or one of the bonds between C-5' and C-6', C-4' and C-5', and C-2 and C-5' together with the dotted line represents a double bond;

with the proviso that the total number of carbon atoms of the compound of formula (I) is 20 or less, e.g. 17, 18 or 19 carbon atoms.

The compounds of formula (I) comprise several chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

In particular embodiments are compounds of formula (I) wherein the relative configuration of the ring system is (1'S, 6'R, 8'S) if the bond C-4' and C-5' together with the dotted line represents a double bond.

Preferred are compounds of formula (I) wherein the bond between C-2 and C-5' together with the dotted line represents a single bond, compounds wherein $R^1$ is hydrogen, methyl or ethyl, and $R^2$ and $R^3$ is hydrogen, and compounds wherein $R^1$ is hydrogen or methyl, Y is a divalent residue of the formula —$CH_2OCH_2$— forming together with the carbon atoms C-2, C-5' and C-4' a six-membered ring system, and the bond between C-4' and C-5' together with the dotted line represents a double bond.

Particularly preferred compounds may be selected from the group of compounds of formula (I) wherein $R^1$ is methyl, Y is —CHO, and the bonds between C-5' and C-6', C-4' and C-5', and C-2 and C-5' are single bonds; $R^1$ is methyl, Y is —CHO, and the bond between C-5' and C-6' or C-4' and C-5' together with the dotted line represents a double bond; $R^1$ is methyl, Y is —CH$_2$OH, and the bonds between C-5' and C-6', C-4' and C-5', and C-2 and C-5' are single bonds; $R^1$ is methyl, Y is —CH$_2$OH, and the bond between C-5' and C-6' or C-4' and C-5' together with the dotted line represents a double bond; $R^1$ is ethyl, Y is —CHO, and the bonds between C-5' and C-6', C-4' and C-5', and C-2 and C-5' are single bonds; $R^1$ is ethyl, Y is —CHO, and the bond between C-5' and C-6' or C-4' and C-5' together with the dotted line represents a double bond; $R^1$ is ethyl, Y is —CH$_2$OH, and the bonds between C-5' and C-6', C-4' and C-5', and C-2 and C-5' are single bonds; $R^1$ is ethyl, Y is —CH$_2$OH, and the bond between C-5' and C-6' or C-4' and C-5' together with the dotted line represents a double bond; $R^1$ is hydrogen and Y is a divalent residue of the formula —CH$_2$OCH$_2$— forming together with the carbon atoms C-2, C-5' and C-4' a six-membered ring system, and the bond between C-4' and C-5' together with the dotted line represents a double bond; and compound of formula (I) wherein $R^1$ is methyl and Y is a divalent residue of the formula —CH$_2$OCH$_2$— forming together with the carbon atoms C-2, C-5' and C-4' a six-membered ring system, and the bond between C-5' and C-6' together with the dotted line represents a double bond.

The compounds of formula (I) may be used alone, as mixtures thereof, or in combination with a base material. As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

The following list comprises examples of known odorant molecules, which may be combined with the compounds of the present invention:

- essential oils and extracts, e.g. tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;
- alcohols, e.g. cinnamic alcohol, cis-3-hexenol, citronellol, Ebanol®, eugenol, farnesol, geraniol, Super Muguet™, linalool, menthol, nerol, phenylethyl alcohol, rhodinol, Sandalore®, terpineol or Timberol®.
- aldehydes and ketones, e.g. anisaldehyde, α-amylcinnamaldehyde, Georgywood™, hydroxycitronellal, Iso E® Super, Isoraldeine®, Hedione®, Lilial®, maltol, Methyl cedryl ketone, methylionone, verbenone or vanillin;
- ethers and acetals, e.g. Ambrox®, geranyl methyl ether, rose oxide or Spirambrene.
- esters and lactones, e.g. benzyl acetate, Cedryl acetate, γ-decalactone, Helvetolide®, γ-undecalactone or Vetivenyl acetate.
- macrocycles, e.g. Ambrettolide, Ethylene brassylate or Exaltolide®.
- heterocycles, e.g. isobutylquinoline.

The compounds according to formula (I) may be used in a broad range of fragrance applications, e.g. in any field of fine and functional perfumery, such as perfumes, household products, laundry products, body care products and cosmetics.

The compounds can be employed in widely varying amounts, depending upon the specific application and on the nature and quantity of other odourant ingredients. The proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in fine perfumery in amounts of from 0.1 to 20 weight percent, more preferably between 0.1 and 5 weight percent. However, these values are given only by way of example, since the experienced perfumer may also achieve effects or may create novel accords with lower or higher concentrations.

The compounds as described hereinabove may be employed into the fragrance application simply by directly mixing the fragrance composition with the fragrance application, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation of a compound of the present invention, as a fragrance ingredient, either by directly admixing the compound to the application or by admixing a fragrance composition comprising a compound of formula (I), which may then be mixed to a fragrance application, using conventional techniques and methods.

As used herein, "fragrance application" means any product, such as fine perfumery, e.g. perfume and eau de toilette; household products, e.g. detergent for dishwasher, surface cleaner; laundry products, e.g. softener, bleach, detergent; body care products, e.g. shampoo, shower gel; and cosmetics, e.g. deodorant, vanishing creme, comprising an odorant. This list of products is given by way of illustration and is not to be regarded as being in any way limiting.

None of the compounds of formula (I), with the exception of 3-(2,2,7,7-tetramethyltricyclo[6.2.1.0$^{1,6}$]undec-5-en-5-yl)propan-2-one, i.e. a compound of formula (I) wherein $R^1$ is hydrogen, Y is —C(CH$_3$)O and the bond between C-5' and C-6' is a double bond, has ever been described in literature, and they are therefore novel. The aforementioned compound has been described by Francis J. McQuillin et al., J. Chem. Research (S), 1977, 61, as an intermediate resulting from the addition of an organic radical to isolongifolene. But the document is silent with regard to its olfactory properties. Thus, the invention provides in another of its aspects a compound of formula (I) as defined hereinabove with the proviso that if $R^1$ is hydrogen and the bond between C-5' and C-6' is a double bond, Y is not —C(CH$_3$)O.

The compounds of the present invention may be prepared starting from the commercially-available isolongifolan-8-one 1 via a suitable 5-alkylidene-2,2,7,7-tetramethyltricyclo[6.2.1.0$^{1,6}$]undecane 2 obtained by Wittig-Horner olefination under conditions known to the person skilled in the art. The latter is then reacted with the corresponding aldehyde of the formula R$^2$CHO according to the usual conditions of the thermal or catalytic Prins reaction to give a mixture of enols of formula 3 and 4 and tetracyclic ethers of formula 5 as shown in scheme 1, which possesses very strong odour notes. The mixtures may be enriched in any of the constituents either by adapting the reaction conditions or by the usual product purification/enrichment processes or by both. Particularly preferred are mixtures comprising about 4 to 90% by weight of each of the compounds 3 and 4 and up to 90% by weight of compound 5. In particular, embodiments are mixtures comprising about 40 to 70 weight % of a compound of the formula 3, about 30 to 50 weight % of a compound of formula 4, and up to 20 weight %, e.g. 0.5 to 10 weight %, of a compound of the formula 5.

Scheme 1:

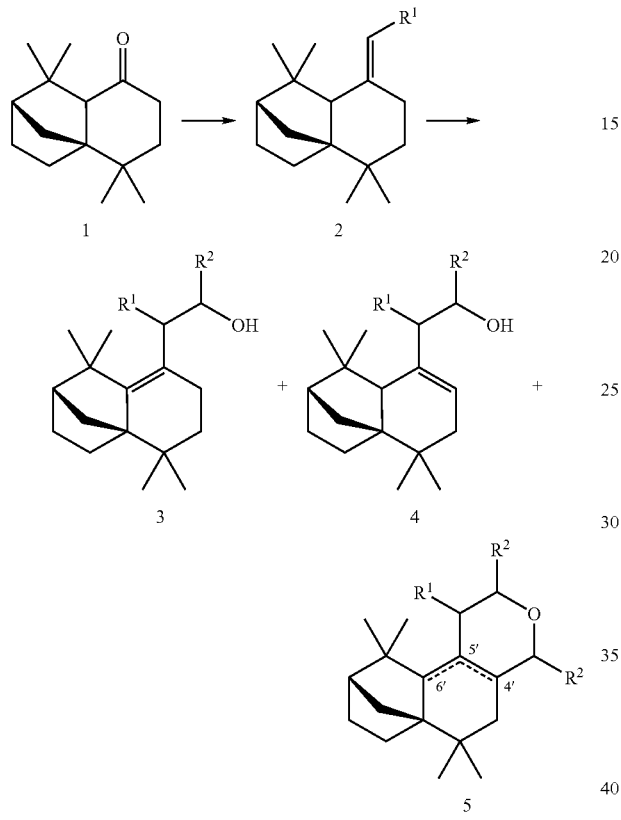

Thus the present invention refers in a further aspect to a fragrance composition comprising a mixture of

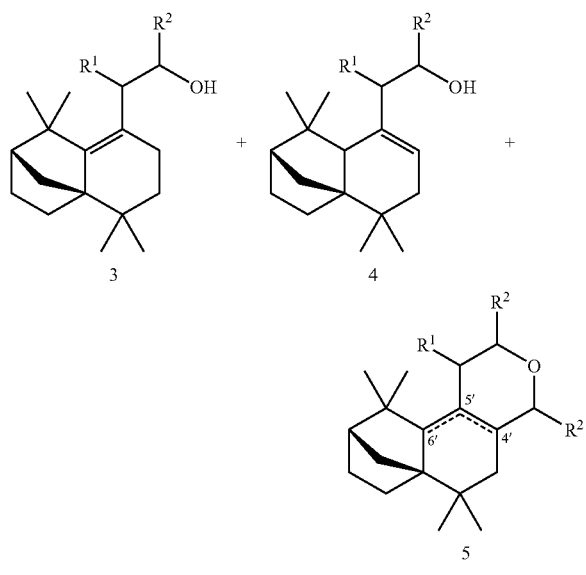

wherein

R$^1$ is hydrogen or C$_1$-C$_3$ alkyl, e.g. methyl, ethyl or isopropyl;

R$^2$ is hydrogen or C$_1$-C$_3$ alkyl, e.g. methyl, ethyl or isopropyl; and in formula 5 the bond between C-5' and C-6' is a single bond and the bond between C-4' and C-5' together with the dotted line represents a double bond; or the bond between C-4' and C-5' is a single bond and the bond between C-5' and C-6' together with the dotted line represents a double bond wherein the mixture comprises a) about 4 to 90 weight % of a compound of formula 3 b) about 4 to 90 weight % of a compound of formula 4; and c) up to about 90 weight % of a compound of formula 5.

The resulting enols 3 and 4 may be further derivatized by simple chemical transformations such as hydrogenation, etherification, isomerization or oxidation under conditions known in the art to give further compounds of formula (I), namely the corresponding aldehydes or acids. The aldehydes and acids may be further reacted with organometallic compounds resulting in secondary alcohols or ketones of formula (I).

The invention is now further described with reference to the following non-limiting examples.

All products described in the Examples were obtained starting from commercially available isolongifolan-8-one (2,2,7,7-tetramethyltricyclo[6.2.1.0$^{1,6}$]undecan-5-one), a mixture of two diastereomeric pairs of enantiomers. Flash chromatography: Merck silica gel 60 (230-400 mesh).

The reported NMR spectra were measured in CDCl$_3$ if not otherwise stated; chemical shifts (δ) are reported in ppm downfield from TMS; coupling constants J in Hz.

EXAMPLE 1

2-(2,2,7,7-Tetramethyltricyclo[6.2.1.0$^{1,6}$]undec-5-en-5-yl)propan-1-ol (3b), 2-(2,2,7,7-tetramethyltricyclo [6.2.1.0$^{1,6}$]undec-4-en-5-yl)propan-1-ol (4b), and 2,2,8,11,11-pentamethyl-6-oxatetracyclo[10.2.1.0$^{1,}$ $_{10}$.0$^{4,9}$]pentadec-9-ene (5b)

a) 5-Ethylidene-2,2,7,7-tetramethyltricyclo[6.2.1.0$^{1,}$ $_6$]undecane (2b)

Potassium tert-butoxide (13.0 g, 0.116 mol) and ethyltriphenylphosphonium bromide (41.6 g, 0.112 mol) were added to a solution of 2,2,7,7-tetramethyltricyclo[6.2.1.0$^{1,6}$]undecan-5-one (1, 20.0 g, 0.091 mol) in cyclohexane (200 ml), the reaction mixture was stirred at room temperature for 78 h and filtered through Celite®. The filtrate was concentrated and distilled under reduced pressure to give (at 95° C./0.1 mbar) 5-ethylidene-2,2,7,7-tetramethyltricyclo[6.2.1.0$^{1,6}$]undecane (2b, 13.1 g, 62% yield, colourless liquid).

$^1$H NMR(C$_6$D$_6$): δ 5.65 (qt, J=6.6, 2.2, 1H), 2.50 (ddd, J=15.0, 4.6, 2.7 1H), 2.18 (m, 1H), 1.81-1.72 (m, 2H), 1.62 (ddd, J=6.6, 2.2, 1.6, 3H), 1.57 (m, 1H), 1.39 (m, 1H), 1.37-1.28 (m, 3H), 1.27-1.19 (m, 1H), 1.23 (s, 3H), 1.16 (ddd, J=13.1,5.0, 2.7, 1H), 1.09 (dd, J=9.5, 1.4, 1H), 1.06 (s, 3H), 1.00 (s, 3H), 0.90 (s, 3H). $^{13}$C NMR(C$_6$D$_6$): δ 138.2 (s), 116.0 (d), 57.4 (s), 54.6 (d), 50.1 (d), 39.3 (s), 37.6 (t), 36.2 (t), 33.7 (q), 33.6 (s), 27.4 (t), 26.8 (q), 25.9 (t), 25.5 (q), 23.4 (q), 21.6 (t), 13.3 (q). MS: 232(M$^+$, 19), 217(23), 203(10), 189(36), 175(12), 161(10), 150(21), 149(100), 147(14), 135(27), 119 (19), 107(28), 105(25), 93(24), 91(34), 79(21), 55(26), 41(29).

b) 2-(2,2,7,7-Tetramethyltricyclo[6.2.1.0$^{1,6}$]undec-5-en-5-yl)propan-1-ol (3b) and 2-(2,2,7,7-tetramethyltricyclo[6.2.1.0$^{1,6}$]undec-4-en-5-yl)propan-1-ol (4b)

Crude 5-ethylidene-2,2,7,7-tetramethyltricyclo[6.2.1.0$^{1,6}$]undecane (2b, ~93% pure, 16.0 g, 0.064 mol) and paraformaldehyde (95% pure, 2.58 g, 0.082 mol) were stirred in an autoclave at 180° C. for 6 h. The reaction mixture was filtered and distilled over a 5 cm Vigreux column to give 6b, a mixture containing 53 and 34.5% of 2-(2,2,7,7-tetramethyltricyclo[6.2.1.0$^{1,6}$]undec-5-en-5-yl)propan-1-ol (3b) and 2-(2,2,7,7-tetramethyltricyclo[6.2.1.0$^{1,6}$]undec-4-en-5-yl)propan-1-ol (4b; two diastereomeric pairs of enantiomers: 30+4.5%) respectively (10.3 g, 61% yield, white slurry); another less pure fraction of the mixture (4.8 g) was isolated but no further purification was carried out. 6b was analytically separated by GC using 30 m×0.25 mm Rtx-Wax column and the odours of the constituents were evaluated by the usual GC/sniff technique.

Odour description (6b=mixture of 3b & 4b (mixture of diastereoisomers)): ambery, woody.

Odour description (4b, main diastereoisomer): ambery, woody, sweet.

Odour description (4b, minor diastereoisomer): ambery, woody.

Odour description (3b): see below.

c) 2-(2,2,7,7-Tetramethyltricyclo[6.2.1.0$^{1,6}$]undec-5-en-5-yl)propan-1-ol (3b)

A sample of the mixture 6b (6.5 g, 0.025 mol) was dissolved in cyclohexane (180 ml), iodine (2.5 g, 9.8×10$^{-3}$ mol) was added, and the resulting suspension was heated at reflux for 24 h. After washing successively with aqueous NaHSO$_3$ and brine, the organic phase was dried (MgSO$_4$), concentrated in vacuo and purified by flash chromatography (MTBE/hexane 1:6) to give 2-(2,2,7,7-tetramethyltricyclo[6.2.1.0$^{1,6}$]undec-5-en-5-yl)propan-1-ol (3b) of acceptable olfactory quality (1.89 g, 29%, slowly solidifying colourless liquid).

$^1$H NMR(C$_6$D$_6$): δ 3.42 (dd, J=10.0, 8.9, 1H), 3.33 (dd, J=10.0, 6.6, 1H), 2.89 (m, 1H), 1.80-1.71 (m, 3H), 1.65-1.58 (m, 2H), 1.44-1.30 (m, 3H), 1.21-1.16 (m, 1H), 1.18 (s, 3H), 1.17 (s, 3H), 1.12 (dd, J=9.5, 1.4, 1H), 1.12-1.05 (m, 1H), 0.92 (s, 3H), 0.87 (d, J=6.9, 3H), 0.86 (s, 3H). $^{13}$C NMR (C$_6$D$_6$): δ 149.2 (s), 125.3 (s), 65.6 (t), 57.4 (s), 49.8 (d), 42.9 (s), 38.0 (d), 36.4 (t), 34.1 (t), 31.3 (s), 29.4 (t), 27.8 (q), 26.5 (q), 26.3 (q), 25.3 (t), 24.4 (q), 20.8 (t), 15.7 (q). MS: 262 (M$^+$, 31), 233(45), 231(100), 219(76), 203(45), 175(81), 161 (28), 147(28), 133(32), 119(45), 105(42), 91(41), 69(28), 55(31), 41(43).

Odour description: ambery, woody.

d) 2-(2,2,7,7-tetramethyltricyclo[6.2.1.0$^{1,6}$]undec-4-en-5-yl)propan-1-ol (4b)

Main diastereoisomer, (1'S*,6'R*,8'S*):

$^1$H NMR δ 5.42 (m, 1H), 3.51-3.44 (m, 1H), 3.40 (dd, J=10.1, 6.1, 1H), 2.49 (sx, J=6.2, 1H), 2.07 (m, 1H), 1.94 (m, 1H), 1.76 (m, 1H), 1.73-1.64 (m, 1H), 1.61 (ddd, J=17.4, 5.6, 1.8, 1H), 1.49-1.39 (m, 1H), 1.38 (m, 1H), 1.30-1.20 (m, 2H), 1.12 (d, J=9.4, 1H), 1.10 (s, 3H), 1.08 (d, J=7.1, 3H), 1.04 (s, 3H), 0.91 (s, 3H), 0.81 (s, 3H). $^{13}$C NMR: δ 140.0 (s), 122.1 (d), 68.3 (t), 55.2 (d), 55.0 (s), 51.0 (d), 39.4 (t), 38.4 (d), 37.7 (s), 36.1 (t), 33.7 (q), 32.6 (s), 26.6 (t), 24.7 (q), 24.1 (q), 23.8 (q), 22.5 (t), 15.7 (q). MS: 262(M$^+$, 38), 233(36), 231 (100), 219(91), 203(62), 175(47), 161(40), 147(34), 133(40), 121(36), 119(56), 105(43), 91(40), 55(33), 41(40).

Minor diastereoisomer, (1'S*,6'S*,8'S*):

$^1$H NMR (C$_6$D$_6$): δ 5.34 (db, J=6.9, 1H), 3.41 (ddd, J=11.0, 7.7, 3.6, 1H), 3.23 (ddd, J=11.0, 5.7, 3.6, 1H), 2.14 (m, 1H), 2.01 (db, J=17.0, 1H), 1.73 (m, 1H), 1.66 (sb, 1H), 1.57-1.45 (m, 4H), 1.33 (m, 1H), 1.11 (s, 3H), 1.08 (d, J=6.9, 3H), 0.99 (db, J=9.6, 1H), 0.95-0.85 (m, 2H), 0.90 (s, 3H), 0.86 (s, 3H), 0.77 (s, 3H). $^{13}$C NMR (C$_6$D$_6$; shifts extracted from HSQC experiment): δ 119.4 (d), 66.8 (t), 56.7 (d), 49.6 (d), 40.7 (d), 39.1 (t), 37.0 (t), 30.1 (t), 29.0 (q), 25.7 (q), 25.6 (q), 25.1 (t), 23.6 (q), 14.6 (q). MS: 262(M$^+$, 57), 247(13), 231(66), 219 (52), 203(85), 201(53), 179(31), 175(30), 163(43), 161(74), 149(60), 133(74), 121(72), 119(100), 105(68), 91(63), 55(46), 41(45).

Odour description: see Example 1b above.

e) 2,2,8,11,11-Pentamethyl-6-oxatetracyclo[10.2.1.0$^{1,10}$.0$^{4,9}$]pentadec-9-ene (5b)

A suspension of 5-ethylidene-2,2,7,7-tetramethyltricyclo[6.2.1.0$^{1,6}$]undecane (2b, 4.0 g, 0.017 mol), paraformaldehyde (2.5 g, 0.079 mol) and montmorillonite K-10 (2.5 g) was refluxed for 2 h, filtered, concentrated in vacuo and purified by flash chromatography (MTBE/hexane 1:15; the crude product contained 37% of 3b and 22.5% of 5b) to afford 2,2,8,11,11-pentamethyl-6-oxatetracyclo[10.2.1.0$^{1,10}$.0$^{4,9}$]pentadec-9-ene (5b, 1.3 g, 27% yield, waxy white solid).

$^{13}$C NMR (C$_6$D$_6$+Cr(acac)$_3$): δ 143.9 (s), 127.5 (s), 74.1 (t), 73.9 (t), 57.3 (s), 49.5 (d), 43.4 (s), 36.9 (2t), 33.9 (d), 32.6 (d), 31.3 (s), 29.3 (t), 28.2 (q), 27.2 (q), 27.0 (q), 25.7 (q), 25.1 (t), 17.7 (q). MS: 274(M$^+$, 40), 259(15), 246(19), 245(100), 231(78), 187(12), 173(17), 159(21), 145(30), 133(16), 119 (25), 105(30), 91(39), 55(26), 41(36).

Odour description: woody, ambery, dry, Iso E-like.

EXAMPLE 2

2-(2,2,7,7-Tetramethyltricyclo[6.2.1.0$^{1,6}$]undec-5-yl)propan-1-ol (7b)

A solution of the mixture 6b (5.0 g, 0.019 mol) in ethanol (25 ml) was hydrogenated in the presence of palladium on activated carbon (10%, 0.55 g), in an autoclave at 110° C. and 60 bar, during 3 h. The catalyst was filtered off, the solvent evaporated in vacuo and the residue (4.5 g) dissolved in cyclohexane (500 ml) and stirred with MCPBA (70%, 4.9 g, 0.020 mol) and NaHCO$_3$ (3.0 g, 0.036 mol) at r. t. for 18 h. After washing successively with aqueous NaHSO$_3$ and brine, the organic phase was dried (MgSO$_4$), concentrated in vacuo and purified by flash chromatography (MTBE/hexane 1:4) to afford a sample of pure 2-(2,2,7,7-tetramethyltricyclo[6.2.1.0$^{1,6}$]undec-5-yl)propan-1-ol (7b, 0.3 g, 6% yield, waxy white solid) and fractions (2.2 g) of 7b+3b, enriched in the saturated alcohol 7b.

$^1$H NMR (C$_6$D$_6$): δ 3.74 (dd, J=9.8, 4.4, 1H), 3.26 (dd, J=9.8, 8.7, 1H), 2.01 (m, 1H), 1.75 (m, 1H), 1.72-1.67 (m, 2H), 1.57 (m, 1H), 1.52 (m, 1H), 1.47-1.40 (m, 2H), 1.38-1.10 (m, 6H), 1.17 (s, 3H), 1.09 (d, J=7.1, 3H), 1.05 (s, 3H), 1.02 (s, 3H), 1.01 (s, 3H). $^{13}$C NMR (C$_6$D$_6$): δ 64.7 (t), 56.0 (s), 50.4 (d), 49.9 (d), 38.0 (d), 37.7 (t), 36.9 (t), 36.8 (d), 33.7 (s), 33.5 (q), 27.1 (t), 27.1 (q), 23.2 (q), 22.1 (t), 21.4 (q), 20.6 (t), 17.1 (q). MS: 264(M$^+$, 6), 249(4), 221(11), 206(18), 205 (100), 177(6), 163(14), 149(26), 135(15), 123(25), 109(67), 107(35), 95(33), 93(31), 81(30), 69(42), 55(36), 41(40).

Odour description (7b): ambery, woody, slightly powdery/earthy.

EXAMPLE 3

5-(1-Methoxyprop-2-yl)-2,2,7,7-tetramethyltricyclo[6.2.1.0$^{1,6}$]undec-5-ene (8b)

A solution of 3b (1.0 g, 3.8×10$^{-3}$ mol) in DMF (5 ml) was added to a THF (8 ml) suspension of sodium hydride (0.27 g of 50% dispersion in mineral oil, washed twice with hexane, 5.6×10$^{-3}$ mol). After 3 h stirring at r. t., methyl iodide (1.6 g, 0.011 mol) was added under cooling and the reaction mixture was stirred at r. t. for additional 4 h, poured into ice-cold 2M HCl (100 ml) and extracted with MTBE (2×100 ml). The organic phase was washed with brine (2×50 ml), dried (MgSO$_4$), concentrated in vacuo and purified by flash chromatography (MTBE/hexane 1:20) to give 5-(1-methoxyprop-2-yl)-2,2,7,7-tetramethyltricyclo[6.2.1.0$^{1,6}$]undec-5-ene (8b, 0.73 g, 69% yield, colourless oil).

$^1$H NMR: δ 3.32 (s, 3H), 3.31-3.22 (m, 2H), 2.98 (m, 1H), 1.88 (ddd, J=17.1, 6.2, 1.4, 1H), 1.78-1.59 (m, 4H), 1.45-1.33 (m, 3H), 1.22-1.16 (m, 1H), 1.21 (s, 3H), 1.17 (dd, J=9.5, 1.4, 1H), 1.13 (s, 3H), 1.08 (m, 1H), 0.98 (d, J=6.8, 3H), 0.90 (s, 3H), 0.82 (s, 3H). $^{13}$C NMR: δ 146.9 (s), 125.6 (s), 76.8 (t), 58.8 (d), 56.8 (s), 49.4 (q), 42.7 (s), 36.1 (t), 35.3 (d), 33.9 (t), 31.1 (s), 29.1 (t), 27.3 (q), 26.3 (q), 26.1 (q), 25.0 (t), 24.1 (q), 21.2 (t), 16.1 (q). MS: 276(M$^+$, 16), 247(6), 232(18), 231(100), 203(10), 175(70), 161(19), 145(13), 133(16), 119(21), 105(21), 91(19), 69(14), 55(13), 45(24), 41(18).

Odour description: earthy/mossy, woody (caryophyllene), floral, spicy, sweet.

EXAMPLE 4

2-(2,2,7,7-Tetramethyltricyclo[6.2.1.0$^{1,6}$]undec-5-en-5-yl)propanal (9b)

Sodium acetate (0.1 g) and PCC (6.6 g, 0.031 mol, portionwise) was added successively at r. t. to a vigorously stirred solution of 3b (6.0 g, 0.023 mol) in dichloromethane (200 ml). After additional 3 h stirring, the black reaction mixture was filtered through Celite®, the filtrate was concentrated in vacuo and purified by flash chromatography (MTBE/hexane 1:10) to give 2-(2,2,7,7-tetramethyltricyclo[6.2.1.0$^{1,6}$]undec-5-en-5-yl)propanal (9b, 3.8 g, 64% yield, white solid).

$^1$H NMR: δ 9.59 (d, J=0.5, 1H), 3.62 (q, J=6.8, 1H), 1.89 (ddd, J=17.4, 6.3, 1.4, 1H), 1.81-1.65 (m, 3H), 1.58 (m, 1H), 1.53-1.37 (m, 3H), 1.27-1.21 (m, 2H), 1.23 (s, 3H), 1.20 (s, 3H), 1.14 (d, J=6.8, 3H), 1.14-1.08 (m, 1H), 0.93 (s, 3H), 0.85 (s, 3H). $^{13}$C NMR: δ 203.5 (d), 152.5 (s), 120.3 (s), 57.5 (s), 49.7 (d), 49.3 (d), 43.1 (s), 36.2 (t), 33.8 (t), 31.0 (s), 29.0 (t), 28.1 (q), 26.1 (q), 25.8 (q), 24.9 (t), 24.1 (q), 22.8 (t), 11.5 (q). MS: 260(M$^+$, 15), 245(2), 232(19), 231(100), 217(21), 203(9), 189(7), 175(79), 161(23), 147(15), 133(21), 119(24), 105(25), 91(28), 69(18), 55(18), 41(25).

Odour description: woody, ambery, floral.

EXAMPLE 5

3-(2,2,7,7-Tetramethyltricyclo[6.2.1.0$^{1,6}$]undec-5-en-5-yl)butan-2-ol (10b)

9b (1.7 g, 6.5×10$^{-3}$ mol) in diethyl ether (50 ml) was added dropwise at 10° C. to a solution of methylmagnesium bromide (3 ml of 3M diethyl ether solution, 9.0×10$^{-3}$ mol) in the same solvent (50 ml). The reaction mixture was stirred at r. t. for additional 2 h, poured into ice-cold 0.1M HCl (100 ml) and extracted with MTBE (100 ml). The organic phase was washed with brine (2×50 ml), dried (MgSO$_4$), concentrated in vacuo and purified by recrystallisation from hexane to afford 3-(2,2,7,7-tetramethyltricyclo[6.2.1.0$^{1,6}$]undec-5-en-5y-1)butan-2-ol (10b, 1.1 g, 61% yield, white prisms, m.p. 119-121° C.).

$^1$H NMR: δ 3.70 (dq, J=9.6, 6.2, 1H), 2.57 (dq, J=9.5, 6.8, OH), 1.89 (ddd, J=17.2, 6.2, 1.1, 1H), 1.79-1.60 (m, 4H), 1.44-1.33 (m, 4H), 1.23-1.18 (m, 1H), 1.20 (s, 3H), 1.16 (s, 3H), 1.20 (d, J=6.3, 3H), 1.09 (d, J=6.7, 3H), 0.91 (s, 3H), 0.81 (s, 3H). $^{13}$C NMR: δ 147.3 (s), 126.0 (s), 70.9 (d), 57.0 (s), 49.6 (d), 43.3 (d), 42.7 (s), 36.0 (t), 33.8 (t), 31.2 (s), 29.1 (t), 27.8 (q), 26.4 (q), 26.1 (q), 25.0 (t), 24.3 (q), 22.5 (q), 21.3 (t), 16.6 (q). MS: 276(M$^+$, 8), 232(20), 231(100), 203(6), 189(7), 176(12), 175(83), 161(22), 133(14), 119(18), 105(18), 91(17), 69(14), 55(12), 45(15), 41(14).

Odour description: ambery, woody, floral, fruity.

EXAMPLE 6

The following compounds listed in Table 1 have been prepared according to the general procedures given in Examples 1 to 5 starting from 5-methylene-2,2,7,7-tetramethyltricyclo[6.2.1.0$^{1,6}$]undecane (2a) and 5-propylidene-2,2,7,7-tetramethyltricyclo[6.2.1.0$^{1,6}$]undecane (2c) respectively. Their odours were evaluated on blotters.

TABLE 1

| Cpd. | R$^1$ is | Y is | —C═C— | Odour description |
|---|---|---|---|---|
| 2c | Et | — | 2, 5' | Woody, agrestic, earthy/mossy |
| 3a | H | —CH$_2$OH | 5', 6' | Ambery, woody, floral, musky |
| 3c | Et | —CH$_2$OH | 5', 6' | Ambery, woody, fruity, powdery |
| 4a | H | —CH$_2$OH | 4', 5' | 4a in a mixture with 3a (68:30.5):Ambery, woody (ionone), musky, powdery, agrestic |
| 4c | Et | —CH$_2$OH | 4', 5' | 4c in a mixture with 3c (44.5:55.5):Ambery, woody, powdery, green |
| 5a | H | —CH$_2$OCH$_2$— | 4', 5' | Musky, fruity, woody, slightly Cashmeran ®-type |
| 8a | H | —CH$_2$OMe | 5', 6' | Ambery, woody, agrestic, musky |
| 8c | Et | —CH$_2$OMe | 5', 6' | Woody (caryophyllene), earthy/mossy, sweet, floral (rosy) |

Compound 2c:

$^1$H NMR: δ 2.45 (ddd, J=14.7, 4.6, 3.0, 1H), 2.11 (m, 1H), 2.10-1.92 (m, 2H), 1.82-1.68 (m, 2H), 1.58 (m, 1H), 1.39 (ddt, J=9.6, 3.0, 1.8, 1H), 1.34-1.15 (m, 4H), 1.20 (s, 3H), 1.11 (dd, J=9.4, 1.5, 1H), 1.02 (2s, 6H), 0.95 (t, J=7.3, 3H), 0.89 (s, 3H). $^{13}$C NMR: δ 136.9 (s), 123.9 (d), 57.2 (s), 54.0 (d), 49.7 (d), 39.2 (s), 37.7 (t), 36.0 (t), 33.6 (q), 33.5 (s), 27.0 (t), 26.7 (q), 26.0 (t), 25.4 (q), 23.4 (q), 21.2 (t), 20.9 (t), 14.9 (q). MS: 246(M$^+$, 36), 231(41), 217(17), 203(72), 190(13), 175(26), 164(28), 163(100), 149(36), 147(26), 133(23), 121 (32), 119(30), 107(68), 105(45), 93(45), 91(59), 79(41), 55(58), 41(75).

Compound 3a:

$^1$H NMR: δ 3.75-3.64 (m, 2H), 2.44-2.32 (m, 2H), 1.95 (ddd, J=17.3, 12.1, 6.3, 1H), 1.84 (ddd, J=17.3, 6.2, 1.0, 1H), 1.75 (m, 1H), 1.70-1.62 (m, 2H), 1.48-1.36 (m, 4H), 1.23 (s, 3H), 1.22-1.16 (m, 2H), 1.12 (s, 3H), 1.11-1.04 (m, 1H), 0.92 (s, 3H), 0.82 (s, 3H). $^{13}$C NMR: δ 150.1 (s), 119.4 (s), 61.4 (t), 57.1 (s), 49.1 (d), 42.7 (s), 36.2 (t), 36.1 (t), 33.9 (t), 31.1 (s), 29.2 (t), 27.4 (q), 26.8 (t), 26.3 (2q), 24.9 (t), 24.3 (q). MS: 248(M$^+$, 33), 233(11), 219(71), 217(16), 205(100), 203(28), 173(22), 161(30), 159(29), 147(23), 131(22), 119(29), 105 (33), 91(35), 41(26).

Compound 3c:
$^1$H NMR: δ 3.62-3.43 (m, 2H), 2.80 (tt, J=8.7, 6.4, 1H), 1.89-1.73 (m, 3H), 1.73-1.65 (m, 2H), 1.48-1.37 (m, 4H), 1.37-1.28 (m, 1H), 1.28-1.18 (m, 2H), 1.25 (s, 3H), 1.18-1.07 (m, 1H), 1.16 (s, 3H), 0.93 (s, 3H), 0.87 (t, J=7.5, 3H), 0.83 (s, 3H). $^{13}$C NMR: δ 151.7 (s), 122.7 (s), 64.6 (t), 57.5 (s), 49.5 (d), 44.5 (d), 42.8 (s), 36.1 (t), 33.6 (t), 31.1 (s), 29.2 (t), 28.3 (q), 26.9 (q), 26.3 (q), 25.1 (t), 24.4 (q), 22.9 (t), 20.4 (t), 11.9 (q). MS: 276(M$^+$, 24), 247(31), 246(20), 245(100), 233(52), 203(36), 189(61), 161(18), 147(24), 133(27), 119(33), 105 (32), 91(33), 69(24), 55(26), 41 (32).

Compound 4a (two diastereomeric pairs of enantiomers (1:1.4); spectra of the major diastereomer):
$^{13}$C NMR: δ 136.5 (s), 122.3 (d), 60.7 (t), 55.6 (d), 55.1 (s), 49.2 (d), 42.3 (s), 39.7 (t), 39.0 (t), 36.7 (t), 32.5 (s), 30.2 (t), 28.5 (q), 25.4 (q), 25.3 (q), 24.7 (t), 23.6 (q). MS: 248(M$^+$, 67), 233(19), 215(24), 205(75), 187(59), 165(40), 150(49), 149(75), 147(81), 133(81), 117(37), 119(84), 105(100), 91(97), 79(50), 55(65), 41(81).

Compound 4c (two diastereomeric pairs of enantiomers (1:2.1); spectra of the major diastereomer)
$^1$H NMR: δ 5.42 (m, 1H), 3.54-3.43 (m, 2H), 2.37 (tt, J=7.3, 4.4, 1H), 2.06 (m, 1H), 1.97 (ddb, J=17.7, 4.8, 1H), 1.76 (m, 1H), 1.73-1.60 (m, 2H), 1.58 (qi, J=7.3, 2H), 1.48-1.41 (m, 1H), 1.37 (m, 1H), 1.36-1.30 (m, 1H), 1.27-1.20 (m, 1H), 1.15-1.11 (m, 1H), 1.08 (s, 3H), 1.06 (s, 3H), 0.94 (t, J=7.3, 3H), 0.91 (s, 3H), 0.81 (s, 3H). $^{13}$C NMR: δ 138.6 (s), 122.3 (d), 65.1 (t), 55.1 (s), 54.4 (d), 51.0 (d), 45.6 (d), 39.4 (t), 37.8 (s), 36.0 (t), 33.8 (q), 32.5 (s), 26.7 (t), 24.7 (q), 24.1 (2q), 22.6 (t), 22.4 (t), 12.4 (q). MS: 276(M$^+$, 20), 247(27), 246(21), 245(100), 233(56), 203(50), 189(41), 161(26), 147 (28), 133(52), 119(67), 105(57), 91(58), 69(34), 55(65), 41(71).

Compound 5a:
$^1$H NMR (C$_6$D$_6$): δ 4.04 (db, J=15.5, 1H), 3.85 (ddd, J=10.7, 5.2, 3.6 1H), 3.80(db, J=15.5, 1H), 3.46 (ddd, J=10.7, 8.9, 3.8, 1H), 2.16 (m, 1H), 1.80-1.69 (m, 2H), 1.57-1.52 (m, 2H), 1.52-1.41 (m, 2H), 1.40-1.30 (m, 2H), 1.05 (s, 3H), 0.99 (d, J=15.1, 1H), 0.97-0.93 (m, 1H), 0.94 (s, 3H), 0.92 (m, 1H), 0.84 (s, 3H), 0.75 (s, 3H). $^{13}$C NMR: (C$_6$D$_6$): δ 127.9 (s), 126.4 (s), 69.2 (t), 64.8 (t), 58.4 (d), 55.3 (s), 49.5 (d), 42.7 (s), 39.0 (t), 37.0 (t), 32.7 (s), 30.6 (t), 30.4 (t), 28.4 (q), 25.5 (2q), 25.0 (t), 23.4 (q). MS: 260(M$^+$, 40), 245(5), 231(5), 217(24), 177(100), 161(19), 133(30), 119(15), 105(25), 91(32), 79(17), 55(25), 41(30).

Compound 8a:
$^1$H NMR: δ 3.47-3.35 (m, 2H), 3.34 (s, 3H), 2.43-2.29 (m, 2H), 1.95 (ddd, J=17.3, 12.1, 6.3, 1H), 1.83 (ddd, J=17.3, 6.3, 1.1, 1H), 1.74 (m, 1H), 1.69-1.59 (m, 2H), 1.46-1.35 (m, 3H), 1.22 (s, 3H), 1.21-1.15 (m, 2H), 1.11-1.03 (m, 1H), 1.10 (s, 3H), 0.91 (s, 3H), 0.81 (s, 3H). $^{13}$C NMR: Δ 5148.4 (s), 120.1 (s), 72.4 (t), 58.5 (q), 56.9 (s), 49.1 (d), 42.7 (s), 36.1 (t), 34.1 (t), 33.3 (t), 31.1 (s), 29.1 (t), 27.5 (t), 27.1 (q), 26.3 (q), 26.0 (q), 24.9 (t), 24.2 (q). MS: 263(11), 262(M$^+$, 55), 247(9), 233(83), 219(100), 217(51), 215(25), 203(31), 201(26), 187 (31), 173(52), 161(88), 159(66), 145(49), 131(56), 119(61), 105(72), 91(66), 69(34), 45(73), 41(43).

Compound 8c:
$^1$H NMR: δ 3.34-3.27 (m, 2H), 3.31 (s, 3H), 2.80 (tt, J=9.2, 5.6, 1H), 1.85 (ddd, J=17.2, 6.2, 1.4, 1H), 1.81-1.59 (m, 5H), 1.46-1.29 (m, 4H), 1.24 (s, 3H), 1.23-1.06 (m, 3H), 1.11 (s, 3H), 0.91 (s, 3H), 0.83 (t, J=7.5, 3H), 0.81 (s, 3H). $^{13}$C NMR: δ 148.4 (s), 121.7 (s), 76.8 (t), 58.9 (q), 57.2 (s), 49.4 (d), 42.8 (s), 42.1 (d), 36.0 (t), 33.9 (t), 31.1 (s), 29.2 (t), 27.6 (q), 26.8 (q), 26.4 (q), 25.1 (t), 24.2 (q), 23.2 (t), 21.3 (t), 11.9 (q). MS: 290(M$^+$, 13), 261(5), 246(19), 245(100), 203(11), 189 (60), 175(8), 161(12), 145(14), 133(16), 119(18), 105(18), 91(18), 69(15), 55(14), 45(23), 41(14).

EXAMPLE 7

Woody-hesperidic Fragrance Composition for Eau De Cologne

| | parts by weight |
|---|---|
| Boisambrene Forte (1-(Ethoxymethoxy)-cyclododecane) | 15 |
| Cedarwood oil Texas | 80 |
| Cepionate ® | 75 |
| (Methyl 2-(3-oxo-2-pentylcyclopentyl)acetate) | |
| Coumarin cryst. | 2 |
| Dipropylene glycol (DPG) | 37 |
| Ethyl linalool | 25 |
| Galaxolide ® 50 IPM | 240 |
| (1,3,4,6,7,8-Hexahydro-4,6,6,7,8,8-hexamethyl-cyclopenta-gamma-2-benzopyran) | |
| Georgywood | 75 |
| (cis-1-(1,2,3,4,5,6,7,8-Octahydro-1,2,8,8-tetramethyl-2-naphthalenyl)-ethanone) | |
| cis-3-Hexenyl formiate | 5 |
| cis-3-Hexenol | 15 |
| Iso E Super ® | 200 |
| (7-Acetyl, 1,2,3,4,5,6,7,8-octahydro-1,1,6,7-tetramethyl naphthalene) | |
| Lemon oil Italy | 75 |
| Liffarome ™ (cis-3-Hexenyl methyl carbonate) 10% in DPG | 25 |
| Nerol extra (3,7-Dimethyl octa-2,6-dien-1-ol) | 10 |
| Nonadyl (6,8-Dimethylnonan-2-ol) | 3 |
| Peach pure (5-Heptyldihydro-2(3H)-furanone) 10% in DPG | 15 |
| Tropional | 8 |
| Velvione (Cyclohexadec-5-ene-1-one) | 20 |
| | 925 |

2-(2,2,7,7-Tetramethyltricyclo[6.2.1.0$^{1,6}$]undec-5-en-5-yl)pronpan-1-ol (3b), and 2-(2,2,7,7-tetramethyltricyclo [6.2.1.0$^{1,6}$]undec-4-en-5-yl)propan-1-ol (4b) (53:34.5) obtained according to Example 1b was admixed in DPG to form a 10% solution. Addition of 75 parts of this solution to the above composition brings volume, roundness and diffusion, while keeping the hesperidic freshness of the top note. It enhances the musky ambery character, improves the performance of the woody-ambery drydown, and helps to develop a very attractive and sensual note.

The invention claimed is:
1. A fragrance composition comprising a compound of formula (I)

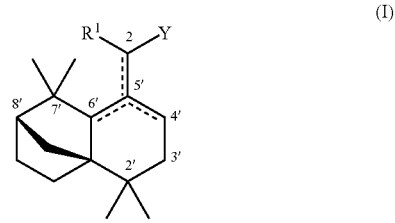

wherein
R¹ is hydrogen or C₁-C₃ alkyl;
Y is a monovalent residue selected from the group consisting of —CR²O and —CHR²OR³,
wherein R² is hydrogen or C₁-C₃ alkyl; and
R³ is hydrogen or C₁-C₃ alkyl; or
Y is a divalent residue of the formula —CHR²OCHR²— forming together with the carbon atoms C-2, C-5' and C-4' a six-membered ring system,
wherein R² is hydrogen or methyl; and
the bonds between C-5' and C-6', C-4' and C-5', and C-2 and C-5' are single bonds;
or one of the bonds between C-5' and C-6', C-4' and C-5', and C-2 and C-5' together with the dotted line represents a double bond;
with the proviso that the total number of carbon atoms of the compound of formula (I) is 20 or less.

2. A fragrance application comprising a compound of formula (I) as defined in claim 1.

3. A method of manufacturing a fragrance application, comprising the step of incorporation a compound of formula (I) as defined in claim 1, to a base material.

4. A fragrance composition comprising a mixture of

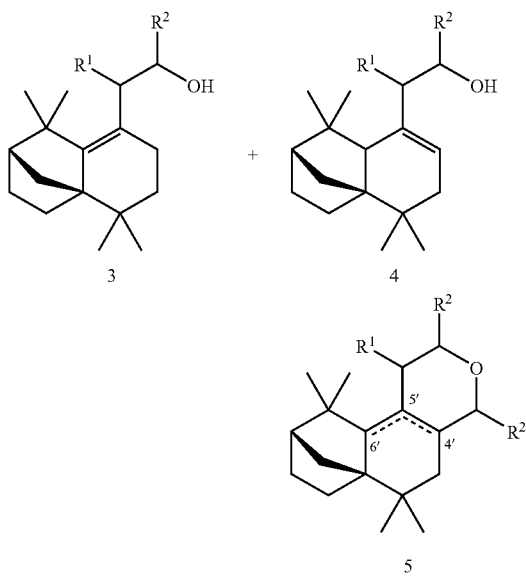

wherein
R¹ is hydrogen or C₁-C₃ alkyl, e.g. ethyl or isopropyl;
R² is hydrogen or C₁-C₃ alkyl, e.g. ethyl or isopropyl; and
wherein in formula 5 the bond between C-5' and C-6' is a single bond and the bond between C-4' and C-5' together with the dotted line represents a double bond; or the bond between C-4' and C-5' is a single bond and the bond between C-5' and C-6' together with the dotted line represents a double bond wherein the mixture comprises
a) about 4 to 90 weight % of a compound of formula 3
b) about 4 to 90 weight % of a compound of formula 4; and
c) up to about 90 weight % of a compound of formula 5.

5. A fragrance application comprising a mixture of compounds 3, 4 and 5 as defined in claim 4.

6. A compound of formula (I)

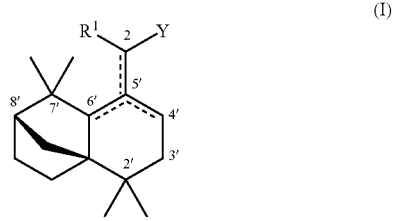

wherein
R¹ is hydrogen or C₁-C₃ alkyl;
Y is a monovalent residue selected from the group consisting of —CR²⁰ and —CHR²OR³,
wherein R² is hydrogen or C₁-C₃ alkyl; and
R³ is hydrogen or C₁-C₃ alkyl; or
Y is a divalent residue of the formula —CHR²OCHR²— forming together with the carbon atoms C-2, C-5' and C-4' a six-membered ring system,
wherein R² is hydrogen or methyl; and
the bonds between C-5' and C-6', C-4' and C-5', and C-2 and C-5' are single bonds;
or one of the bonds between C-5' and C-6', C-4' and C-5', and C-2 and C-5' together with the dotted line represents a double bond;
with the proviso that
I) the total number of carbon atoms of the compound of formula (I) is 20 or less;
II) if R¹ is hydrogen and the bond between C-5' and C-6' is a double bond, Y is not —C(CH₃)O.

7. A compound of formula (I) according to claim 6 wherein the bond between C-4' and C-5' together with the dotted line represents a double bond; and
the relative configuration of the ring system is (1'S, 6'R, 8'S).

8. A compound according to claim 6 selected from:
2-(2,2,7,7-tetramethyltricyclo[6.2.1.0$^{1,6}$]undec-5-en-5-yl)propan-1-ol (3b),
2-(2,2,7,7-tetramethyl-tricyclo[6.2.1.0$^{1,6}$]undec-4-en-5-yl)propan-1-ol (4b),
2,2,8,11,11-pentamethyl-6-oxatetracyclo[10.2.1.0$^{1,10}$.0$^{4,9}$]pentadec-9-ene (5b),
2-(2,2,7,7-tetramethyl-tricyclo[6.2.1.0$^{1,6}$]undec-5-yl)propan-1-ol (7b), 5-(1-methoxyprop-2-yl)-2,2,7,7-tetramethyltricyclo[6.2.1.0$^{1,6}$]undec-5-ene (8b),
2-(2,2,7,7-tetramethyl-tricyclo[6.2.1.0$^{1,6}$]undec-5-en-5-yl)propanal (9b),
3-(2,2,7,7-tetramethyl-tricyclo[6.2.1.0$^{1,6}$]undec-5-en-5-yl)butan-2-ol (10b),
2-(2,2,7,7-tetramethyltricyclo-[6.2.1.0$^{1,6}$]undec-5-en-5-yl)ethanol (3a),
2-(2,2,7,7-tetramethyltricyclo[6.2.1.0$^{1,6}$]undec-5-en-5-yl)butan-1-ol (3c),
2-(2,2,7,7-tetramethyltricyclo[6.2.1.0$^{1,6}$]undec-4-en-5-yl)ethanol (4a),
2-(2,2,7,7-tetramethyltricyclo[6.2.1.0$^{1,6}$]undec-4-en-5-yl)butan-1-ol (4c),
5-(1-methoxyeth-2-yl)-2,2,7,7-tetramethyltricyclo[6.2.1.0$^{1,6}$]undec-5-ene (8a),
5-(1-methoxybut-2-yl)-2,2,7,7-tetramethyltricyclo[6.2.1.0$^{1,6}$]undec-5-ene (8c), and
2,2,11,11-tetramethyl-6-oxatetracyclo[10.2.1.0$^{1,10}$.0$^{4,9}$]pentadec-4(9)-ene (5a).

* * * * *